United States Patent [19]

Onuma et al.

[11] 4,409,814
[45] Oct. 18, 1983

[54] GAS EXTRACTING DEVICE

[75] Inventors: Hideo Onuma; Shigeo Kobayashi, both of Yokohama, Japan

[73] Assignee: Tokyo Shibaura Denki Kabushiki Kaisha, Kawasaki, Japan

[21] Appl. No.: 232,354

[22] Filed: Feb. 6, 1981

[51] Int. Cl.³ .............................................. G01N 31/00
[52] U.S. Cl. ........................................................ 73/19
[58] Field of Search ............................. 73/19, 23, 23.1

[56] References Cited

U.S. PATENT DOCUMENTS

| | | | |
|---|---|---|---|
| 3,673,853 | 7/1972 | Griswold et al. | 73/19 |
| 3,844,160 | 10/1974 | Yamaoka | 73/19 |
| 4,164,137 | 8/1979 | Williamson | 73/19 |
| 4,236,404 | 12/1980 | Ketchum et al. | 73/19 |

Primary Examiner—Stephen A. Kreitman
Attorney, Agent, or Firm—Oblon, Fisher, Spivak, McClelland & Maier

[57] ABSTRACT

A gas extracting device for extracting gas suspended in a liquid from the liquid including a vessel for separating gas suspended in the liquid from the liquid, a mechanism for storing the gas, a mechanism for drawing in the gas from the vessel and for exhausting the gas to the gas storing mechanism, a mechanism for actuating the mechanism for drawing in and exhausting the gas, a vacuum pump connected to the vessel, the gas storing mechanism and the mechanism for drawing in and exhausting the gas and an assembly for selectively intercommunicating the vessel, the mechanism for drawing in and exhausting the gas, the gas storing mechanism and the vacuum pump.

8 Claims, 1 Drawing Figure

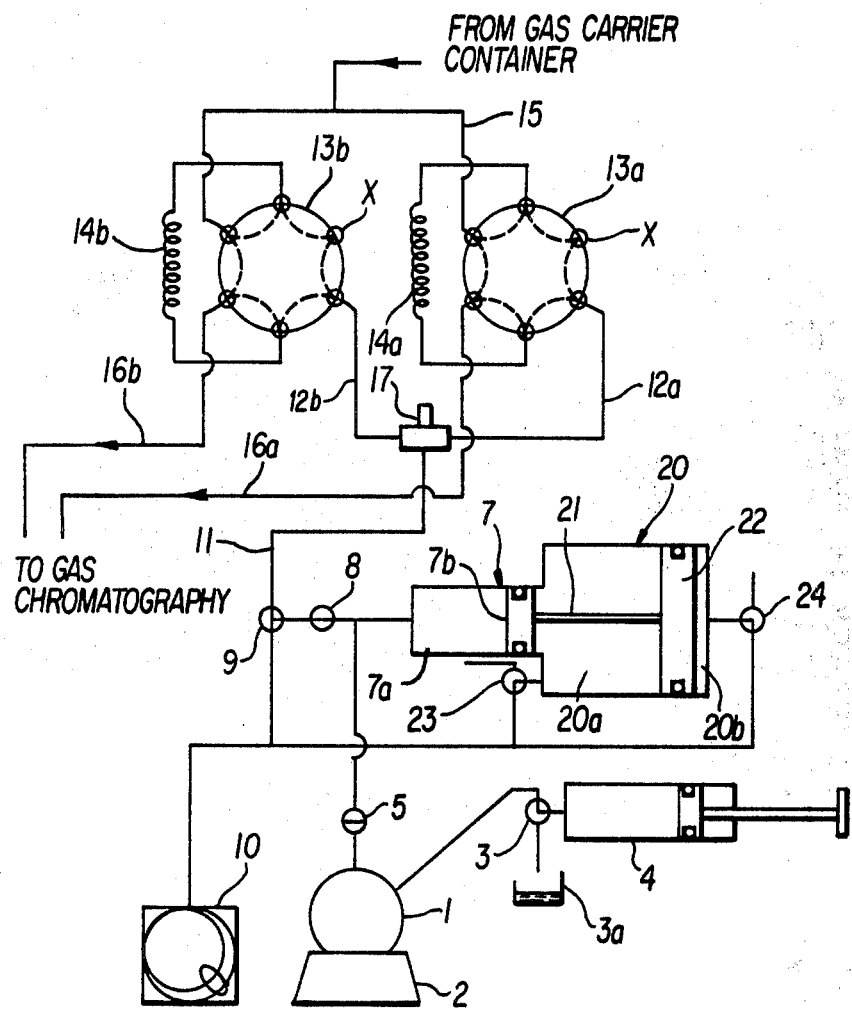

GAS EXTRACTING DEVICE

BACKGROUND OF THE INVENTION

1. Field of the Invention

This invention generally relates to a gas extracting device which is used to analyze gas suspended or dissolved in a liquid, such as an insulating oil, in order to check the abnormal state of an electric apparatus regarding electric power of a transformer, reactor etc., using the insulating oil.

2. Description of the Prior Art

In general, there are typically three types of gas extracting devices for extracting gas suspended in the insulating oil., ine., a Torricelli's vacuum type, a combination of a mercury diffusion pump and Toepler pump type, and a combination of a vacuum pump and a moving valve type of gas extracting device.

In the Torricelli's vacuum type gas extracting device, the so-called Torricelli's vacuum is first produced by using a level bottle made of glass filled with the mercury, and forcing a gas suspended in the insulating oil to be extracted into a vessel made of glass which is vacuum state. Due to usage of mercury and the vessel made of glass, this device is accordingly inconvenient in that scattering of mercury and damage to the glass vessel may occur as a result of an accident.

Moreover, in the mercury diffusion pump and Toepler pump type of gas extracting device, by using an oil rotary pump, a mercury diffusion pump and a Toepler pump, the interior of a desired vessel made of glass is first maintained in a vacuum state. Then, by injecting the insulating oil into the desired vessel, the gas suspended in the oil is extracted and stored in a gas accumulating vessel. There is, however, some danger of the mercury scattering and the vessel being damaged as could occur in the above-mentioned Toricelli's vacuum type device.

Furthermore, in the third type, i.e., the vacuum pump and moving valve type of gas extracting device, the interior of a vessel, i.e., a cylinder, is first maintained in a vacuum state by the vacuum pump. After completely extracting the gas into the cylinder, the gas is guided into a gas accumulating tube by operation of the moving valve. However, the moving valve, i.e., the piston coupled with the cylinder, can only be moved once by switching over the valves associated with and mounted on both sides of the cylinders because pressures at both ends of cylinder chamber become equal. Accordingly, it is difficult to fully extract the gas highly suspended in the oil and to measure the quantity of the suspended gas with accuracy.

Furthermore, besides the three types above mentioned, there is also known a carrier gas replacing type of gas extracting device in which the gas in the insulating oil is drawn out from the oil by directly injecting the carrier gas into the oil, or by bubbling the carrier gas. In the case where a low concentration of suspended gas being present it is, however, difficult to measure the quantity of suspended gas with accuracy because of the relatively small quantity of insulating oil to be analyzed which can be obtained at one time.

SUMMARY OF THE INVENTION

Accordingly, it is one object of this invention to provide a new and improved gas extracting device in which highly suspended gas in the liquid, or a gas with high solubility can be fully extracted with high efficiency.

Another object of this invention is to provide a new and improved gas extracting device in which the dangers of damage to glass and mercury scattering as mentioned above is avoided since it need not involve the use of the glass device filled with mercury.

Briefly, in accordance with one aspect of this invention, a gas extracting device is provided which includes a gas extracting device for extracting gas suspended in a liquid from the liquid including a vessel for separating gas suspended in the liquid from the liquid, a mechanism for storing the gas, a mechanism for drawing in the gas from the vessel and for exhausting the gas to the gas storing mechanism, a mechanism for actuating the mechanism for drawing in and exhausting the gas, a vacuum pump connected to the vessel, the gas storing mechanism and the mechanism for drawing in and exhausting the gas and an assembly for selectively communicating the vessel, the mechanism for drawing in and exhausting the gas, the gas storing mechanism and the vacuum pump.

BRIEF DESCRIPTION OF THE DRAWINGS

A more complete appreciation of the invention will be readily obtained as the same becomes better understood by reference to the following detailed description when considered in connection with the accompanying drawing, wherein:

The sole FIGURE is a block diagram of a gas extracting device according to this invention.

DETAILED DESCRIPTION OF THE PREFERRED EMBODIMENTS

Referring now to the sole FIGURE, one preferred embodiment of a gas extracting device in accordance with this invention is shown as including an evacuated vessel 1 in which air has been removed and the insulating oil therein to be analyzed is stirred by a stirring member 2 on which the vessel 1 is mounted in order to stir the oil in the vessel and to separate the gas from the oil.

The stirring member, for example a magnetic stirrer 2 preferably constitutes an iron piece to be accommodated in vessel 1 and a magnetic device which produces a rotating magnetic field to make the iron piece in the vessel revolve.

A three way switching valve 3, having a drain container or reservoir 3a, which can be connected with a sample injector 4, is connected with vessel 1.

Vessel 1 is also connected through a valve 5 with a cylinder chamber 7a of a reciprocation type piston device 7 with a piston 7b, the cylinder chamber 7a being connected through a valve 8 and a three way switching valve 9 with a vacuum pump 10.

On the other hand, a conductor tube 11, connected with the three way switching valve 9, is connected with a plurality of branched conductor tubes (two pipes 12a and 12b), each branch conductor tube 12a and 12b being connected through switching valves 13a and 13b with gas accumulating tubes 14a and 14b, respectively.

A conductor tube 15, connected with a carrier gas container (not shown) filled with the carrier gas is connected to a gas analyzer, for example a gas chromatograph (not shown) analyzer through switching valves 13a and 13b and conductor tubes 16a and 16b.

When the position of the switching valves 13a and 13b is in a first position, the gas in the conductor tube 11 is conducted into the gas accumulating tubes 14a and 14b, but the carrier gas in the conductor tube 15 is interrupted by switching valves 13a and 13b.

When the position of the switching valves 13a and 13b is in a second position, the gas in the conductor tube 11 is interrupted by switching valves 13a and 13b, but the gas conducted in gas accumulating tubes 14a and 14b is carried by the carrier gas from the carrier gas container to the gas chromatograph analyzer.

The number of sets including a branch conductor tube 12, a switching valve 13 and a gas accumulating tube 14 depends on the kind and the number of gases to be analyzed.

In the embodiment according to this invention, there are two sets, one of which is communicated with the gas chromotograph analyzer to analyze several gases, for example $H_2$, $O_2$, $N_2$, $CH_4$ and $CO$ and the other of which is communicated with the gas chromatograph analyzer to analyze several gases, for example $CO_2$, $C_2H_2$, $C_2H_4$ and $C_2H_6$.

A pressure sensor 17 provided on the conductor tube 11 serves to measure the quantity of the gases supplied to the gas accumulating tubes 14a and 14b via the conductor tube 11 in accordance with the well-known relationship equation of Boyle-Charles' law between the pressure value and the volume value.

An actuating mechanism, or a differential piston device 20, which actuates the reciprocation type of piston device 7, will now be explained. A piston 22 having a larger diameter than that of piston 7b is coupled with piston 7b through a piston rod 21. Both of cylinder chambers 20a and 20b of the differential piston device 20 are connected with vacuum pump 10 through three way switching valves 23 and 24, respectively, one end of three way switching valves 23 and 24 being opened to the atmosphere.

The differential piston device 20 is driven by the difference in pressure between vacuum and atmosphere. Namely, by changing the three way switching valves 23 and 24 so as to make the chamber 20a connect to the atmosphere and to make chamber 20b connect to vacuum pump 10, piston 22 is moved from the leftward position to the rightward position in the FIGURE. As a result, since the piston 7b has been moved in accordance with the movement of the piston 22, the gas from vessel 1 via valve 5 is drawn into chamber 7a. On the other hand, by changing three way switching valves 23 and 24 so as to make chamber 20a connect to vacuum pump 10 and to make chamber 20b connect to atmosphere, piston 20 is moved from the rightward position to the leftward position in the FIGURE. As a result, since piston 7b is moved in accordance with the movement of piston 22, the gas drawn into chamber 7a is discharged to gas accumulating tubes 14a and 14b through valve 8, three way switching valve 9, conductor tube 11 and switching valves 13a and 13b.

It should be understood that the gas suspended in the liquid is extracted from vessel 1 to gas accumulating tubes 14a and 14b. By repeating the actuation of the reciprocating piston, the highly suspended gas in the liquid can be easily extracted.

In operation, three way switching valve 3 provided between the evacuated vessel 1 and sample injector 4 filled with the insulating oil to be analyzed is changed so as to make sample injector 4 open to the atmosphere and a part of the insulating oil in sample injector 4 is discharged to drain container 3a to draw out the air from the connection part around switching valve 3.

After vacuum pump 10 is communicated with chamber 7a via valves 9 and 8, evacuated vessel 1 via the valve 5 and the gas accumulating tubes 14a and 14b via valves 9, 13a and 13b, vacuum pump 10 is operated until the interior communicated with pump 10 reaches a predetermined vacuum state.

In this case, piston 7b is beforehand positioned at the rightward position in the FIGURE, in which the volume in the chamber 7a is the greatest, by the operation of differential piston device 20, both of the three way switching valves 23 and 24 being maintained so as to communicate between vacuum pump 10 and chambers 20a and 20b in order to stop the movement of the piston 22.

When the interior communicated with pump 10 reaches the determined vacuum state, three way switching valve 9 is changed so as to not communicate between pump 10, chamber 7a and gas accumulating tubes 14a and 14b in order to start the transfer of the gases from vessel 1 to chamber 7a and the gas accumulating tubes 14a and 14b.

At the same time, by changing three way switching valve 3 so as to communicate between sample injector 4 and vessel 1, the insulating oil in injector 4 is transferred into vessel 1, the insulating oil in vessel 1 being stirred by magnetic stirrer 2 to make the gas suspended in the oil easily separate from the oil.

As a result, the gas, separated from the insulating oil by means of the magnetic stirrer, is communicated to and stored in chamber 7a and gas accumulating tubes 14a and 14b. In order to forcibly discharge the gas in chamber 7a to the gas accumulating tube, valve 5 is closed, and piston 7b is moved from the rightward position to the leftward position in the FIGURE by means of actuation of differential piston device 20. Accordingly, the gas in chamber 7a is transferred to gas accumulating tubes 14a and 14b.

When the transfer of the gas to tubes 14a and 14b is completed as mentioned above, at that time valve 8 is closed, and piston 7b of reciprocation type piston device 7 is then again moved from the leftward position to the rightward position by means of differential piston device 20.

As a result, since the interior of cylinder chamber 7a again is under a vacuum state, by opening valve 5 the gas separated from the insulating oil in evacuated vessel 1 is stored in chamber 7a again. The gas stored in chamber 7a is in turn transferred to gas accumulating tubes 14a and 14b by repeating operation from closing valve 5 to the movement of the piston 7b.

It should be thus understood that even gas with high solubility and which is hard to extract from the liquid is extracted by repeating the operation of the drawing in and discharging operation mentioned above with high efficiency.

The quantity of gas withdrawn from vessel 1 is measured by pressure sensor 17, which is calibrated in advance, in the manner mentioned above. By changing switching valves 13a and 13b from the first position to the second position, the gas filled in gas accumulating tubes 14a and 14b is transferred to the gas chromatograph (not shown) via conductor tubes 16a and 16b to analyze by the carrier gas from the carrier gas container (not shown).

It should now be apparent that in accordance with the teachings of this invention that even gas with high solubility is fully extracted from the vessel containing the liquid to be analyzed by repeating the operation of the piston in the reciprocation type of the piston device as compared with the prior devices.

That is to say, in such a prior device, the number of times repeating of the operation of the piston occurs is only one time because both ends of the chambers of the piston reach the same pressure i.e., a vacuum state. Therefore, the piston can move neither in a righward nor leftward position.

In the embodiment according to this invention, since the actuating device, which actuates the piston to extract the gas transferred from the vessel to the gas accumulating device, is provided, repeating of the piston movement can be carried out.

Moreover, in this embodiment which employs the additional actuating device, to actuate the piston for drawing in and discharging the gas, for example the differential piston device according to this invention, since the source of additionally actuating device., i.e., vacuum, can be utilized with vacuum pump 10, it is not necessary to provide a particular device to drive an additional actuating device, for example the differential piston device.

As will therefore be apparent, this invention also provides a gas extracting device which does not require a great deal of space in general and is accordingly compact and light. Furthermore, according to this invention it is possible to avoid the danger of the mercury scattering and the vessel being damaged as mentioned above since mercury is not used to extract the gas from the liquid within which the gas is suspended.

Obviously, many modifications and variations of this invention are possible in light of the teachings of this invention. Thus, although this invention has been explained by way of example with the employment of a differential piston device driven by the vacuum pump, it should be apparent that, if desired, the differential piston device could be changed to the well known crank mechanism driven by the motor, or the well known reciprocation mechanism and the like. It is therefore to be understood that within the scope of the appended claims, the invention may be practiced otherwise than as specifically described herein.

What is claimed as new and desired to be secured by Letters Patent of the United States is:

1. A gas extracting device for extracting gas suspended in a liquid from the liquid, comprising;
    vessel means for separating gas suspended in the liquid from the liquid,
    means for storing the gas,
    means for drawing in the gas from the vessel means and for exhausting the gas to the gas storing means, said means for drawing including a piston device comprising a disk and cylinder wherein said disk is movable reciprocally in said cylinder,
    means for actuating the means for drawing in and exhausting the gas, said actuating means comprising a second piston device which is larger than said first piston device and includes a second disk and a second cylinder wherein said second disk is movable reciprocally in said cylinder,
    a vacuum pump connected to the vessel means, the gas storing means, and the means for drawing in and exhausting the gas, and
    means for selectively intercommunicating the vessel means, the means for drawing in and exhausting the gas, the gas storing means and the vacuum pump, whereby said gas is extracted from said vessel means to said means for storing by repeated actuation of said piston device and repeated actuation of said means for selectively intercommunicating.

2. A gas extracting device according to claim 1, further comprising injecting means connected to the vessel means for injecting the liquid to be measured to the vessel means.

3. A gas extracting device according to claim 1, the actuating means being connected to the vacuum pump to drive the actuating means.

4. A gas extracting device according to claim 3, the piston device being mounted on the axial line of the second piston device, and the first disk of the first piston device is rigidly connected with the second disk of the second piston device.

5. A gas extracting device according to claim 1, further comprising means for stirring the liquid in the vessel means.

6. A gas extracting device according to claim 5, the stirring means comprising a magnetic stirrer mounted on the vessel, and a magnetic piece connected to said magnetic stirrer to stir the liquid in the vessel.

7. A gas extracting device according to claim 1, further comprising a gas analyzer, the gas storing means comprising means for accumulating the gas from the means for drawing in and exhausting the gas, means for passing a carrier gas to be transferred to said gas analyzer, and means for selectively changing the accumulating means into said means for passing the carrier gas.

8. A gas extracting device according to claim 7, further comprising a pressure sensor mounted between the accumulating and the means for passing the carrier gas.

* * * * *